(12) United States Patent
Arwari et al.

(10) Patent No.: US 12,167,904 B2
(45) Date of Patent: Dec. 17, 2024

(54) TEMPERATURE SENSOR PATCH AND SYSTEM

(71) Applicants: Biotags, LLC, Key Biscayne, FL (US); University of Miami, Miami, FL (US)

(72) Inventors: Brian Arwari, Coral Gables, FL (US); Luis Carlos Diaz Bautista, Bucaramanga (CO)

(73) Assignees: Biotags, LLC, Key Biscayne, FL (US); University of Miami, Miami, FL (US)

( * ) Notice: Subject to any disclaimer, the term of this patent is extended or adjusted under 35 U.S.C. 154(b) by 526 days.

(21) Appl. No.: 17/237,612

(22) Filed: Apr. 22, 2021

(65) Prior Publication Data

US 2021/0330190 A1   Oct. 28, 2021

Related U.S. Application Data

(60) Provisional application No. 63/013,594, filed on Apr. 22, 2020.

(51) Int. Cl.
| | |
|---|---|
| *A61B 5/00* | (2006.01) |
| *A61B 5/01* | (2006.01) |
| *A61B 90/98* | (2016.01) |

(52) U.S. Cl.
CPC .............. *A61B 5/01* (2013.01); *A61B 5/0008* (2013.01); *A61B 90/98* (2016.02); *A61B 5/6833* (2013.01); *A61B 2562/0271* (2013.01); *A61B 2562/08* (2013.01)

(58) Field of Classification Search
CPC ......... A61B 5/01; A61B 5/0008; A61B 90/98; A61B 5/6833; A61B 2562/0271; A61B 2562/08; A61B 2560/0412; H01Q 1/2225; H01Q 9/285
See application file for complete search history.

(56) References Cited

U.S. PATENT DOCUMENTS

| | | | | |
|---|---|---|---|---|
| 6,975,834 B1 * | 12/2005 | Forster | ................. | H01Q 1/2225 |
| | | | | 455/279.1 |
| 7,354,195 B2 * | 4/2008 | Sakano | ................. | G01K 1/024 |
| | | | | 374/E1.004 |
| 7,448,874 B2 * | 11/2008 | Willis | ................. | G01K 1/02 |
| | | | | 374/E13.002 |
| 7,474,230 B2 * | 1/2009 | Blom | ................. | G01K 7/01 |
| | | | | 340/539.22 |

(Continued)

OTHER PUBLICATIONS

Amendola, S. et al., "Design, Calibration, and Experimentation of an Epidermal RFID Sensor for Remote Temperature Monitoring," IEEE Sensors Journal, IEEE Service Center, New York, NY, USA, vol. 16, No. 19, pp. 7250-7257 (Oct. 1, 2016).

(Continued)

*Primary Examiner* — May A Abouelela
(74) *Attorney, Agent, or Firm* — Koenig IP Works, PLLC; Katherine Koenig

(57) ABSTRACT

Devices, systems, and methods for remotely and, optionally, continuously, reading a temperature of an object, such as a human. In one embodiment, a temperature sensor patch comprises: a sensor circuit, the sensor circuit including: a radiofrequency identification (RFID) chip; and an antenna; and a layer of base material, the sensor circuit being in the layer of material and the layer of base material being configured to permit a signal transfer between the sensor circuit and a surrounding environment.

16 Claims, 9 Drawing Sheets

(56) References Cited

U.S. PATENT DOCUMENTS

| | | | | |
|---|---|---|---|---|
| 7,625,117 | B2* | 12/2009 | Haslett | A61B 5/01 |
| | | | | 374/111 |
| 7,688,182 | B2* | 3/2010 | Nagai | G06K 19/0723 |
| | | | | 342/51 |
| 7,857,507 | B2* | 12/2010 | Quinn | G01J 5/025 |
| | | | | 374/45 |
| 8,412,317 | B2* | 4/2013 | Mazar | A61B 5/0205 |
| | | | | 600/547 |
| 9,451,897 | B2* | 9/2016 | Mazar | A61B 5/6833 |
| 9,560,975 | B2* | 2/2017 | Mei | G06K 19/07773 |
| 9,693,689 | B2* | 7/2017 | Gannon | A61B 5/0008 |
| 9,709,445 | B2* | 7/2017 | Caldara | A61B 5/01 |
| 10,034,609 | B2* | 7/2018 | Sun | G01K 1/08 |
| 10,225,890 | B2* | 3/2019 | Bourke, III | H05B 6/062 |
| 10,327,703 | B2* | 6/2019 | Niederauer | A61B 5/14552 |
| 10,390,759 | B2* | 8/2019 | Quinn | A61B 5/002 |
| 10,420,473 | B2* | 9/2019 | Shi | A61B 5/6833 |
| 10,451,489 | B2* | 10/2019 | Bousquet | G01K 7/01 |
| 10,739,205 | B2* | 8/2020 | Jang | G01K 1/143 |
| 10,849,501 | B2* | 12/2020 | Gannon | A61B 5/01 |
| 11,212,916 | B2* | 12/2021 | Edmundson | H05K 1/118 |
| 11,330,711 | B2* | 5/2022 | Edmundson | H05K 3/38 |
| 11,369,313 | B2* | 6/2022 | Kim | G01D 21/02 |
| 11,515,594 | B2* | 11/2022 | Furutani | H01M 50/136 |
| 2004/0032377 | A1* | 2/2004 | Forster | G06K 19/07786 |
| | | | | 343/793 |
| 2009/0234200 | A1* | 9/2009 | Husheer | A61B 10/0012 |
| | | | | 600/301 |
| 2012/0229270 | A1* | 9/2012 | Morley | A61B 5/6806 |
| | | | | 340/539.12 |
| 2012/0316458 | A1* | 12/2012 | Rahman | A61B 5/6802 |
| | | | | 600/549 |
| 2013/0030259 | A1* | 1/2013 | Thomsen | A61B 5/4824 |
| | | | | 600/301 |
| 2014/0121557 | A1 | 5/2014 | Gannon et al. | |
| 2016/0183794 | A1* | 6/2016 | Gannon | G01K 1/024 |
| | | | | 600/549 |
| 2016/0328584 | A1* | 11/2016 | Rokhsaz | G06K 7/10326 |
| 2017/0110796 | A1* | 4/2017 | Rokhsaz | H01Q 1/2216 |
| 2018/0040939 | A1 | 2/2018 | Rokhsaz et al. | |
| 2018/0184903 | A1 | 7/2018 | Wood et al. | |
| 2020/0244104 | A1* | 7/2020 | Katajamaki | H04B 5/79 |
| 2022/0121898 | A1* | 4/2022 | Yamamoto | H01Q 9/30 |
| 2022/0188590 | A1* | 6/2022 | Sugimoto | H01Q 1/2225 |
| 2022/0188592 | A1* | 6/2022 | Sugimoto | H01Q 9/285 |

OTHER PUBLICATIONS

Bhattacharyya, Rahul et al., "RFID Tag Antenna Based on Temperature Sensing," 2010 IEEE International Conference on RFID, Piscataway, NJ, USA, pp. 8-15 (Apr. 14, 2010).

Gmih, Yassine et al., "Compact Antenna for UHF-RFID Tag Tested on the Human Body for Identification Cards," International Journal of Intelligent Engineering and Systems, vol. 13, No. 1, pp. 227-236 (Feb. 2020).

International Search Report (PCT/ISA/210), dated Sep. 6, 2021, issued by European Patent Office for PCT/US2021/028663 (4 pages).

Shi, Xianwei et al., "A Passive Temperature-Sensing Antenna Based on a Bimetal Strip Coil," Sensors, vol. 17, No. 4, p. 665 (Mar. 23, 2017).

Zhang, Jun et al., "A Review of Passive RFID Tag Antenna-Based Sensors and Systems for Structural Health Monitoring Applications," Sensors, vol. 17, No. 2, p. 265 (Jan. 29, 2017).

* cited by examiner

TEMPERATURE SENSOR PATCH AND SYSTEM

CROSS-REFERENCE TO RELATED APPLICATIONS

This application is related to and claims the benefit of U.S. Provisional Patent Application Ser. No. 63/013,594, filed Apr. 22, 2020, entitled TEMPERATURE MONITORING SYSTEMS AND DEVICES, the entirety of which is incorporated herein by reference.

TECHNICAL FIELD

This disclosure relates to devices, systems, and methods for remotely reading a temperature of an object, such as a human. This disclosure also relates to devices, systems, and methods for contact tracing, data storage, digital payment, and activity logging and communication across partner networks.

BACKGROUND

Public safety is an increasingly important concern, and one that is addressed by the installation and/or use of detection and alert systems. For example, metal detectors and identity verification systems are becoming a common sight in airports, schools, hospitals, amusement parks, and other public locations.

Additionally, public health is rapidly becoming a primary, and often, critical, consideration. As a consequence of the recent coronavirus pandemic, reading the temperature of each person entering a public location, such as a government building, airport, hospital, media gathering, or the like is a prevalent strategy for detecting symptomatic and/or mildly symptomatic carriers of the disease. For example, an elevated temperature reading may indicate the person has been infected with COVID-19, and therefore should be refused entry and isolated for further examination and/or to prevent transmission of the virus to others. However, this requires close proximity or, in some instances, contact between the person being tested and the person operating the thermometer or temperature reading device. Also, this can be a time-consuming process and capable of testing only a few people per minute. Thus, it is not a practical technique for testing large crowds, for reducing or eliminating contact with infected or possibly infected individuals, and for continuously monitoring the condition of individuals and/or groups.

RFID technology is used in a variety of fields, including temperature sensing. Particular frequencies are more appropriate for certain applications; for example, high frequency (HF) RFID of 1-14 MHz effectively penetrates biological materials, which is why the 13.56 MHz bandwidth is used in anti-shoplifting devices. However, such frequencies can only travel a short distance. Ultra-high frequency (UHF) RFID, on the other hand, may be advantageous in that signals can travel much farther, the signal can potentially carry much more information, and it uses much less power than lower frequencies. For at least this reason, the global use of UHFRFID technology is increasing. However, UHF RFID signals lose power and get dispersed in anything with a high water content or metallic surface. Additionally, RFID tags include antennas that become de-tuned when applied to metallic surfaces or to objects with a high water content. Antennas are designed to transmit a signal through the air. When mounted on a surface, such as a wall, the antenna includes a ground plate designed to electromagnetically isolate the antenna from the surface beneath, to reduce or eliminate interference between the material and the antenna. However, the disadvantage of a ground plate is that it makes the antenna much larger, typically twenty times the surface area.

The interference of an antenna by a substrate can significantly reduce the performance of the antenna, possibly all the way to zero, which phenomenon is referred to as "de-tuning." Different materials will affect an antenna in different ways. For example, Styrofoam has almost no effect (that is, Styrofoam is not a "lossy" material), whereas metal or water will de-tune an antenna all the way down to practically zero performance (that is, these materials are "very lossy"). Thus, depending on the material on which the antenna is mounted, a ground plane or spacer (buffer material) may be required to preserve antenna function.

Biological tissue such as skin has a high water content and relatively high dielectric characteristics (compared to air); therefore, UHF RFID tags and other antennas do not work on skin, or will experience de-tuning (in some cases, a complete loss of function). Antennas used on a lossy medium like skin typically will include isolation layer(s) from the skin and/or added battery to improve signal strength.

SUMMARY

Some embodiments advantageously provide devices, systems, and methods for remotely and, optionally, continuously, reading a temperature of an object, such as a human. In particular, the devices, systems, and methods disclosed herein may be used to remotely and continuously monitor temperatures in real time of many people in an area to quickly and accurately detect abnormal temperatures, or temperatures surpassing a threshold value. Additionally, the devices and systems disclosed herein are usable on or in direct contact with human skin, without the need for a ground plate or spacer material and without requiring a battery or other power source.

In one embodiment, a passive temperature sensor patch comprises: a sensor circuit, the sensor circuit including: a radiofrequency identification (RFID) chip; and a dipole antenna; and a layer of base material, the sensor circuit being in the layer of base material and the layer of base material being configured to permit a signal transfer between the sensor circuit and a surrounding environment.

In one aspect of the embodiment, the RFID chip is an ultra-high frequency (UHF) RFID chip. In one aspect of the embodiment, the RFID chip is tuned to use a UHF ISM band of 902 to 1028 MHz.

In one aspect of the embodiment, the dipole antenna includes a first pole and a second pole, each of the first and second poles having a width of approximately 33 mm and a height of approximately 34 mm. In one aspect of the embodiment, the sensor circuit further includes a plurality of inductors extending between the first and second poles. In one aspect of the embodiment, each of the plurality of inductors has a length of approximately 10.2 mm. In one aspect of the embodiment, a distance between outermost inductors of the plurality of inductors is approximately 10.3 mm.

In one aspect of the embodiment, the sensor circuit is configured such that a gain of the antenna is optimal (maximal) when the passive temperature sensor patch is affixed to a biological material. In one aspect of the embodiment, the biological material is a multilayered substrate. In one aspect of the embodiment, the multilayered substrate includes: a first layer that is skin; a second layer that is subcutaneous tissue; a third layer that is muscle; and a fourth layer that is bone.

In one aspect of the embodiment, the sensor circuit is configured such that the antenna has a gain of at least −8.4 dB.

In one aspect of the embodiment, the temperature sensor patch further comprises a coating layer on at least one surface of the layer of base material.

In one aspect of the embodiment, the RFID chip is configured to store personal identification data, monetary data, logistical data, access authorization data, medical data, and/or ticketing data.

In one embodiment, a passive temperature monitoring system comprises: a temperature sensor patch including: a sensor circuit having a radiofrequency (RFID) chip and a dipole antenna; and a layer of base material, the sensor circuit being in the layer of base material and the layer of base material being configured to permit a signal transfer between the sensor circuit and a surrounding environment; and a reader unit including: at least one antenna, the at least one antenna being configured to send and receive radiofrequency signals to and from the temperature sensor patch; and a central processing unit (CPU), the CPU being programmed to correlate a temperature sensor code value in a radiofrequency signal received from the passive temperature sensor patch to a temperature.

In one aspect of the embodiment, the passive temperature sensor patch is configured to be affixed to a skin of a wearer, the correlated temperature being a temperature of the wearer's skin. In one aspect of the embodiment, the CPU is programmed to calculate a core temperature of the wearer based on the temperature of the wearer's skin.

In one aspect of the embodiment, the processing circuitry is programmed to: record a plurality of instantaneous temperatures over time; calculate a baseline average temperature over time based on the plurality of instantaneous temperatures over time; compare a new instantaneous temperature to the baseline average temperature over time; and generate an alert if the new instantaneous temperature exceeds the baseline average temperature over time.

In one aspect of the embodiment, the new instantaneous temperature and the baseline average temperature over time are from a same wearer.

In one aspect of the embodiment, the new instantaneous temperature and the baseline average temperature over time are from different wearers.

In one aspect of the embodiment, the CPU is programmed to transmit temperature data to at least one partner entity.

BRIEF DESCRIPTION OF THE DRAWINGS

A more complete understanding of embodiments described herein, and the attendant advantages and features thereof, will be more readily understood by reference to the following detailed description when considered in conjunction with the accompanying drawings wherein.

DETAILED DESCRIPTION

Figure 1:
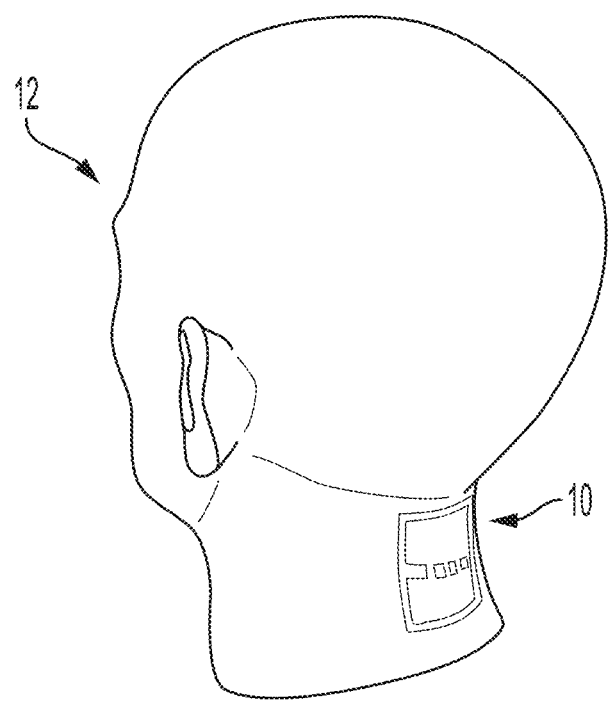
FIG. 1 shows an exemplary temperature sensor patch worn on a neck of a user, in accordance with the present disclosure.

Before describing in detail exemplary embodiments, it is noted that the embodiments reside primarily in combinations of apparatus components and steps related to remotely reading and monitoring temperature of objects, such as humans. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

In general, the temperature sensor patch disclosed herein includes an antenna design that allows the temperature sensor patch to be placed directly on the user's skin, a lossy material due to high water content, without the need for a ground plane or buffer material therebetween. Currently known antennas are designed to achieve maximum aerial propagation of signals, and any distortions caused by substrate materials must be mitigated by the use of a ground plane or buffer material. In contrast, the antenna of the temperature sensor patch disclosed herein is purposely designed as a poor aerial antenna. The natural dielectrical properties of skin, which cause lossyness and de-tuning, are considered and countered in the design of the presently disclosed antenna so the antenna performs without the need for further corrections. That is, distortions are produced when the temperature sensor patch is used on skin, but the antenna is designed such that the antenna functions more efficiently when used on skin. Surprisingly, it becomes a better antenna when used on skin, rather than a worse one. Additionally, by allowing direct contact with the skin, sensors connected to the antenna may also be in direct contact with the skin. In turn, this permits the transmission of physiological data collected from the skin such as temperature, blood oxygen levels, body composition, skin conductance, and others. Other currently known devices are able to measure these physiological characteristics by separating the sensor from the antenna and using power to transmit the data. In contrast, the temperature sensor patch of the present disclosure allows for a completely passive antenna and device that requires no battery or power source.

Referring now to the figures in which like reference designators are used for like elements, an exemplary temperature sensor patch 10 worn on a neck of a wearer 12 is shown in FIG. 1. The temperature sensor patch 10 is configured to be thin and nearly unnoticeable by the wearer, and can be manufactured for little cost. The temperature sensor patch 10 is configured to be adhered, affixed, mounted to, or otherwise attached to a surface or substrate such as human skin. For example, the temperature sensor patch 10 may be configured to be adhered to the back of a wearer's neck (as shown in FIG. 1), under a wearer's arm, on a wearer's temple proximate the temporal artery, on a wearer's wrist, or at another suitable location. Further, as discussed in greater detail below, in one embodiment the temperature sensor patch is configured to take advantage of the dielectric properties of human skin to boost antenna function.

The temperature sensor patch 10 disclosed herein combines the ability to measure skin temperature using RFID with the ability to identify and distinguish each of a plurality of temperature sensor patches using a unique identifier (UID).

Figure 2:
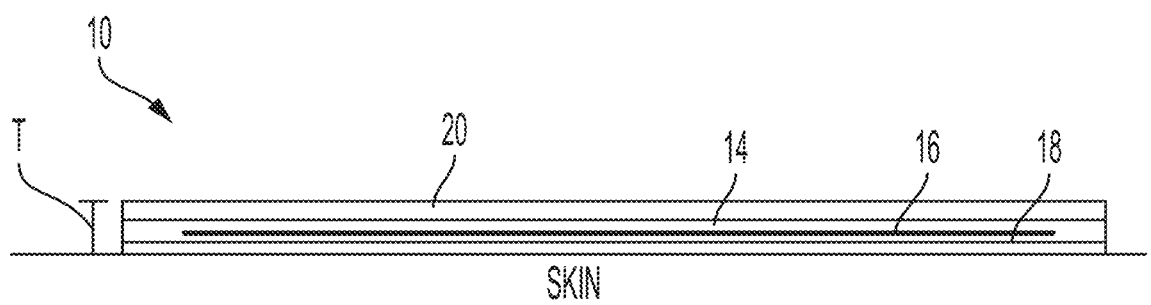
FIG. 2 shows a schematic cross-sectional view of an exemplary temperature sensor patch, in accordance with the present disclosure.

Referring now to FIG. 2, in one embodiment the temperature sensor patch 10 includes at least one layer: a first layer that is a base material layer 14 composed of a thin, flexible material (for example, plastic, silicone, polymer, polyvinylchloride (PVC), polyethylene terephthalate (PET), polyesters, or the like) that includes a sensor circuit 16. In one embodiment, the sensor circuit 16 includes an electrically conductive material that is overlaid, deposited, printed, or otherwise added or adhered to the base material layer 14. The sensor circuit 16 is shown in FIG. 2 as being within (that is, not on an outer surface of) the active layer for illustration; however, it will be understood that the sensor circuit 16 may be in or on any part of the base material layer 14, including integrated within the base material layer 14 itself and/or on an outer surface of the base material layer 14. For comparison with the multilayered substrate 22 (see Table 1 below), the dielectric constant of a layer of PET having a thickness (height) of approximately 0.05 mm is 3.4. In some embodiments, at least one surface of the base material layer 14 is composed of or includes (for example, is integrated with) an adhesive material. In one non-limiting example, the adhesive material is capable of adhering to human skin and remaining adhered for up to at least three days and, in some embodiments, without causing discomfort or skin irritation. Alternatively, in some embodiments, the temperature sensor patch 10 further includes a second or adhesive layer 18 adhered, affixed, or otherwise attached to a first surface of the base material layer 14, and the adhesive layer 18 is composed of or includes the adhesive material. In one embodiment, the sensor circuit 16 lies between two layers of base material (such as PET) to form the base material layer 14 with sensor circuit 16 therein, and the adhesive layer 18 lies between the adhesive layer 18 and an optional sacrificial layer (such as paper or other removable covering to protect the adhesive layer 18 until use). Regardless of whether the adhesive material is part of the base material layer 14 or the adhesive layer 18, any material between the sensor circuit and the wearer's skin, including adhesive and/or the material of the base material layer, is thin enough to permit signal transfer (for example, thermal transfer) between the wearer and the sensor circuit in the active layer. In some embodiments, the temperature sensor patch is configured such that at least a portion of the sensor circuit is in direct contact with the wearer's skin. Put another way, in one embodiment the base material layer 14 is configured to permit at least one surface of the sensor circuit 16 to be in communication with a surrounding environment (for example a wearer's skin) and to be affected by the dielectric and thermal properties of that surrounding environment.

Continuing to refer to FIG. 2, in some embodiments the temperature sensor patch 10 optionally includes a coating layer (superstrate) 20 that is adhered, affixed, or otherwise attached to a second surface of the base material layer 14 opposite the first surface. The material, thickness, and other characteristics of the coating layer 20 may be chosen based on the application or intended use of the temperature sensor patch 10. For example, in one non-limiting example, the coating layer 20 may be configured (such as material and/or thickness) to provide thermal insulation to the sensor circuit 16 of the base material layer 14, such as when the temperature sensor patch 10 is to be used in cold climates. Additional embodiments may include a coating layer 20 that is configured to protect the sensor circuit 16 against ultraviolet light, corrosion, temperature extremes, or the like, and/or the coating layer may be configured to provide aesthetic or other functional features to the temperature sensor patch, such as color (for example, to match the user's skin tone or to be an appealing color for children), texture (for example, to reduce friction), waterproofing, text (for example, instructions), advertising (for example, logos and websites), or the like. The coating layer 20 is a radiofrequency-translucent material that allows radiofrequency (RF) waves to pass therethrough to the base material layer 14. Additionally, the base material layer 14 and/or the coating layer 20 may be composed of or include metamaterials.

Figure 3:
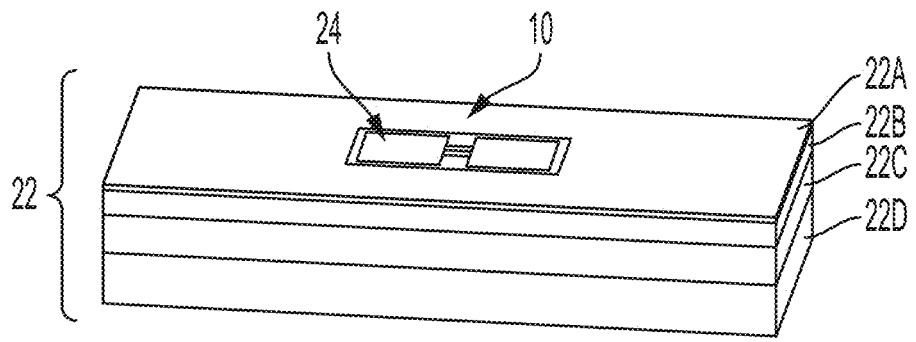
FIG. 3 shows an exemplary temperature sensor patch affixed to skin, in accordance with the present disclosure.

Referring now to FIG. 3, an exemplary temperature sensor patch 10 is shown affixed to a multilayered substrate 22 such as human tissue, although it will be understood that the temperature sensor patch may be affixed to other surfaces or tissues of other animals, such as pigs, cows, chickens, or the like. In the non-limiting example shown in FIG. 3, the multilayered substrate 22 includes at least one layer of skin 22A (which may further include an epidermal layer and a dermal layer), at least one layer of subcutaneous tissue 22B (for example, including fat), at least one layer of muscle 22C, and at least one layer of bone 22D. However, it is also contemplated that the multilayered substrate 22 may include more or fewer layers. As shown in FIG. 3, the temperature sensor patch 10 is affixed to the outermost layer, the skin 22A. In some embodiments, the base material layer 14 mechanically or physically supports the sensor circuit 16 within the temperature sensor patch 10 and the multilayered substrate 22 functions, or at least partially functions, as the substrate for the antenna 24 of the sensor circuit 16. As such, the dielectric properties of the multilayered substrate 22 may affect the electrical performance of the antenna 24.

Figure 4:
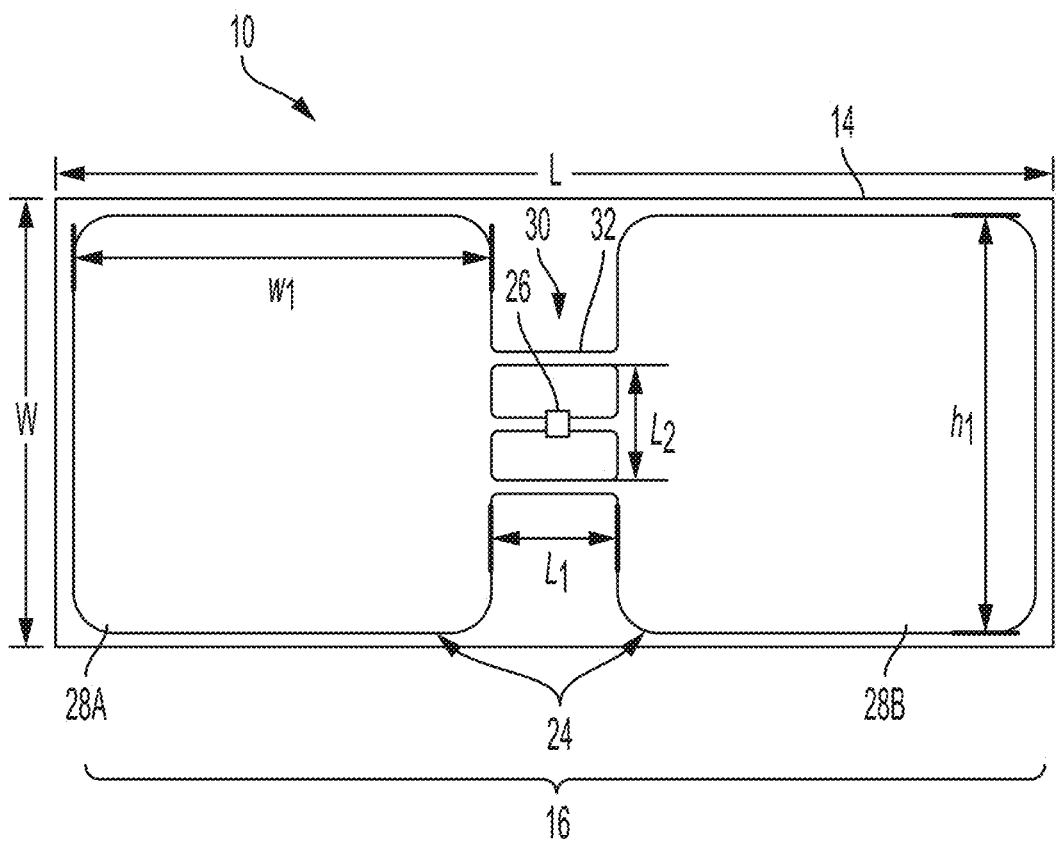
FIG. 4 shows an exemplary temperature sensor patch, in accordance with the present disclosure.
Figure 5:
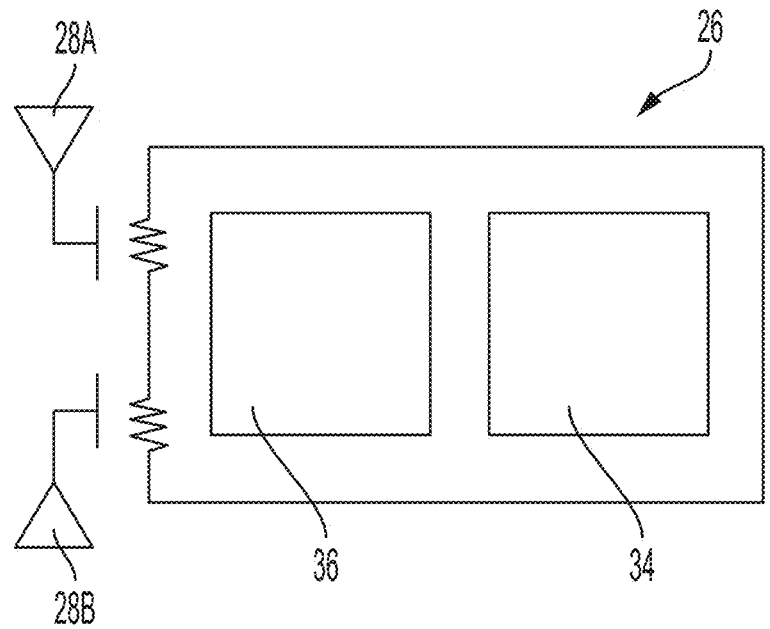
FIG. 5 shows a schematic view of an exemplary RFID chip, in accordance with the present disclosure.

Referring now to FIG. 4, and with reference to FIG. 5, an exemplary temperature sensor patch 10 is shown in greater detail. In one embodiment, the temperature sensor patch 10 functions as a passive RFID tag (that is, is a passive temperature sensor patch) and includes the sensor circuit 16. The sensor circuit 16 generally includes a radiofrequency identification (RFID) chip 26 and an antenna 24. In one embodiment, the antenna is a dipole antenna that includes two conductive elements (for example, a first pole 28A and a second pole 28B) positioned a distance from each other. For example, a dipole antenna topology may be chosen because of its differential excitation in a single-layer layout. In such an embodiment, the first and second poles 28A, 28B are in communication with a bridge 30 therebetween that includes at least one inductor 32 that conveys power from the antenna poles 28A, 28B to the RFID chip 26. In one embodiment, the RFID chip 26 is tuned to use an ultra-high frequency (UHF) industrial, scientific, and medical (ISM) frequency band of between 902 and 928 MHz. The antenna 24 and inductor(s) 32 are composed of an electrically conductive material, such as aluminum, copper, silver, or other suitable material. In one embodiment, the RFID chip 26 includes an integrated circuit that includes at least one memory 34 configured to read and write data, and may optionally include an ability to lock with a password and/or other features or components. In some embodiments, the integrated circuit also includes at least one controller 36. In some embodiments, the integrated circuit may use both RFID and near-field communication (NFC) technology. In one embodiment, the sensor circuit 16 harvests energy from a reader unit 38 and does not require an internal power source (such as a battery) to detect temperature and/or temperature changes.

Continuing to refer to FIG. 4, in one embodiment, during operation the sensor circuit 16 is a passive circuit in which the RFID chip 26 harvests power from the reader unit 38 through the antenna 24 when an electromagnetic field impinges the sensor circuit 16. With this power, the sensor circuit 16 returns data (for example, identification data, temperature data, event log data, and/or the like) to a remote reader unit 38 (shown in FIGS. 9-12). In one non-limiting example, the temperate sensor patch 10 may transmit signals to a reader unit 38 that is located over 1.5 meters away. Further, the RFID chip 26 functions as a temperature sensor element that is configured to measure temperature of skin to which it is affixed.

Continuing to refer to FIG. 4, the RFID chip 26 and the antenna 24 are electrically matched to obtain a satisfactory performance of the temperature sensor patch 10. Some currently known RFID tags include auto-tuning circuits that compensate for any mismatch between the RFID chip and the antenna. This is a useful feature when the resonance of the antenna is shifted due to, for example, impedance changes related to the different surfaces on which the RFID tag may be located or affixed. However, this auto-tuning capability is constrained to materials that exhibit similar dielectric properties among them. Typically, an RFID tag located on or affixed to a "lossy" medium such as skin or other biological tissue will include one or more isolation layers (for example, a ground plane or buffer material) between the sensor circuit and the medium to which the RFID tag is affixed. However, such isolation layers add complexity and introduce thermal constraints. Further, in some embodiments, the temperature sensor patch 10 disclosed herein is configured such that the sensor circuit 16 is located as close as possible to the skin to achieve accurate skin temperature measurements. In one non-limiting example, the sensor circuit 16 is positioned within the base material layer 14 such that a very thin layer of base material (for example, 0.1 mm±0.05 mm) separates the sensor circuit 16 from the wearer's skin. Thus, in some embodiments, the sensor circuit 16 is located within or embedded within the base material layer 14.

Thus, the temperature sensor patch 10 disclosed herein incorporates the biological tissues to which the temperature sensor patch 10 is affixed as layers of the substrate. That is, the dielectric properties of the biological tissue (for example, as shown in FIG. 3) are taken into account when designing at least the antenna 24. Consequently, the antenna 24 of the temperature sensor patch 10 disclosed herein is designed such that it is a poor aerial antenna; however, the antenna function (gain) is optimized when the temperature sensor patch 10 is affixed to a substrate having predictable, or at least substantially predictable, dielectric properties (that is, having dielectric properties that are predictable within a certain range). If the antenna 24 were designed for optimal function when not used on a lossy medium such as the multilayered substrate 22, the impedance mismatch between the antenna 24 and the multilayered substrate 22 would adversely affect radiation impedance when the temperature sensor patch 10 were in use. Unlike currently used antennas/sensor circuits, the geometry of the sensor circuit 16, including the antenna 24, is such that the antenna 24 performs poorly when used in the air or on a substrate that is less lossy than the multilayered substrate 22.

It has been found that the maximum radiation efficiency is obtained when the dipole length of the antenna is half of the effective wavelength. In some embodiments, this wavelength is calculated with the central operation frequency, 915 MHz, and the effective dielectric constant of the multilayered substrate 22. In one study, a dielectric characterization based on a microstrip resonator of a finite length was made of biological tissues of multiple human individuals. The average of the dielectric properties of these biological tissues is shown in Table 1. The half wavelength obtained with the multilayered substrate was 76.2 mm.

TABLE 1

Dielectric properties of the multilayered substrate.

| Tissue | Height (mm) | Dielectric constant ($\epsilon_r$) | σ [s/m] |
| --- | --- | --- | --- |
| Skin | 1 | 32 | 0.35 |
| Fat | 12 | 5 | 0.05 |
| Muscle | 15 | 55 | 1 |
| Bone | 20 | 20 | 0.05 |

The multilayered substrate 22 cannot be absolute, due to normal variations between individuals in properties such as tissue thickness. Therefore, in some embodiments, the sensor circuit 16 of the temperature sensor patch 10 disclosed herein (for example, the RFID chip 26) includes an auto-tuning circuit that is configured to compensate or adjust for dielectric differences in the skin between multiple individuals, while the gross impedance matching is attained using the averaged multilayered model.

In light of these considerations, an exemplary sensor circuit configuration is shown in FIG. 4. In one non-limiting example, the temperature sensor patch 10 has a rectangular shape with a length L of approximately 80 mm (±2 mm), a width W of approximately 36 mm (±2 mm), and a thickness T of approximately 1.0 mm (±0.2 mm) (thickness T shown in FIG. 2). In one embodiment, each pole 28A, 28B of the antenna 24 has a rectangular, or at least substantially rectangular, shape having a width $w_1$ and a height $h_1$. In one non-limiting example, the width $w_1$ is approximately 33 mm (±1 mm) and the height $h_1$ is approximately 34 mm (±1 mm). However, it will be understood that the temperature sensor patch 10 may have any suitable size, shape, and configuration and is not necessarily limited to those configurations shown and described herein. In one embodiment, the bridge 30 includes a plurality of inductors 32 spanning a distance $L_1$ between the first and second poles 28A, 28B of the antenna 24. In one non-limiting example, the distance $L_1$ is approximately 10.2 mm (±0.2 mm). Further, in one embodiment a distance $L_2$ between the two outermost of the plurality of inductors 32 is approximately 10.3 mm (±0.2 mm). This geometry of the sensor circuit allows for optimization of the antenna gain even when the temperature sensor patch 10 is affixed to a lossy medium such as the multilayered substrate 22.

Figure 6:
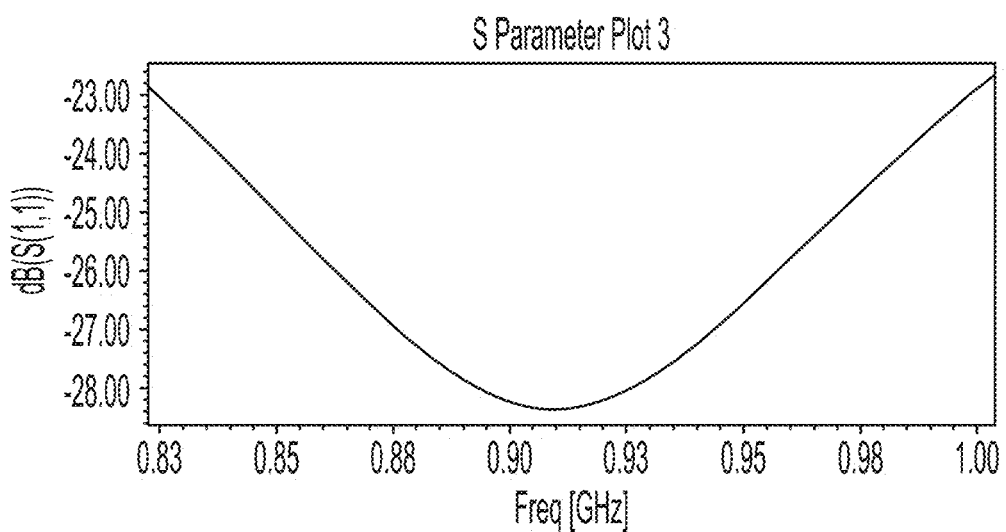
FIG. 6 shows a chart illustrating an exemplary scattering parameter (s-parameter plot) of an exemplary temperature sensor patch, in accordance with the present disclosure.
Figure 7:
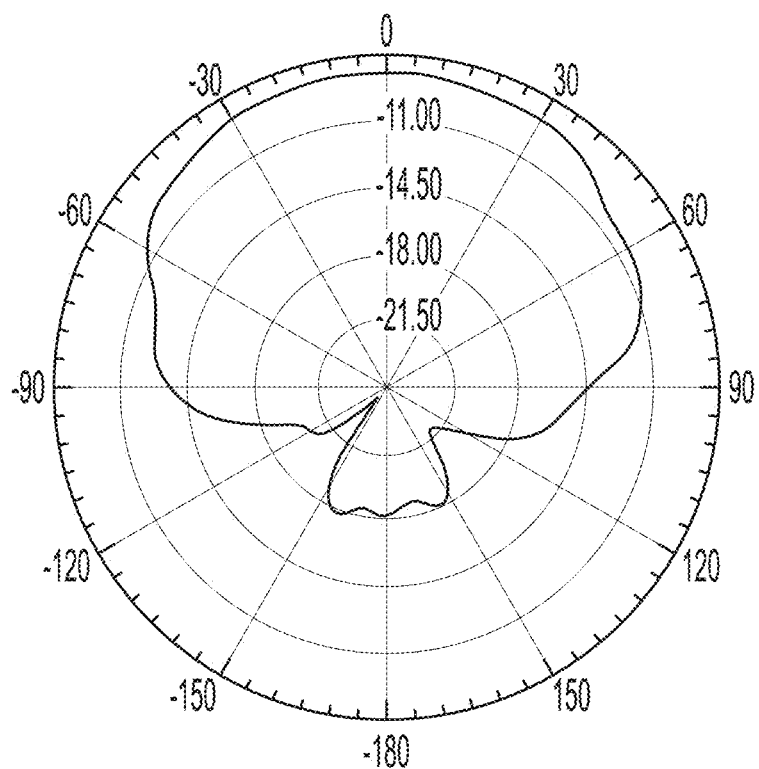
FIG. 7 shows an E-plane radiation pattern of the temperature sensor patch at 915 MHz, in accordance with the present disclosure.
Figure 8:
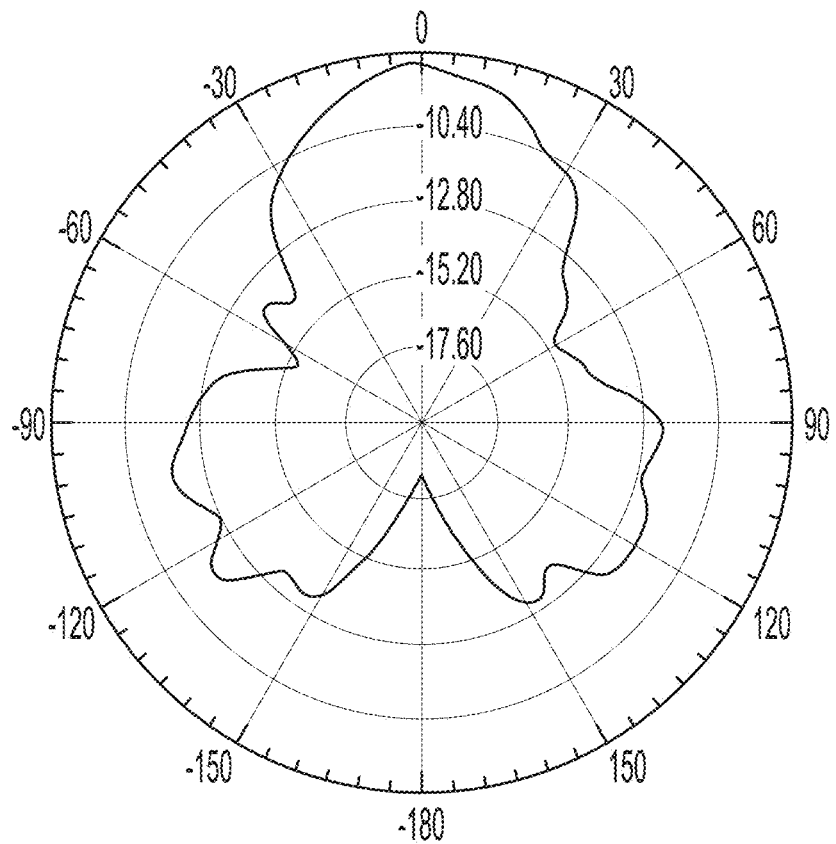
FIG. 8 shows an H-plane radiation pattern of the temperature sensor patch at 915 MHz, in accordance with the present disclosure.

Referring now to FIGS. 6-8, the sensor circuit design shown in FIG. 4 displays excellent performance across the full UHF band, as show in FIG. 6. In some embodiments, the unique antenna design disclosed herein may work well with commercially available integrated circuits (for example, but not limited to, the Magnus™ S3 integrated circuit (Azxon, Austin, TX). In some embodiments, the antenna has a gain of at least −8.4 dB. The radiation patterns of the antenna 24 of the temperature sensor patch 10 disclosed herein are plotted in FIG. 7 for E-plane and in FIG. 8 for H-plane at 915 MHz. Both patterns show that the maximum gain is located at $\varphi=0$, $\theta=0$.

Figure 9:
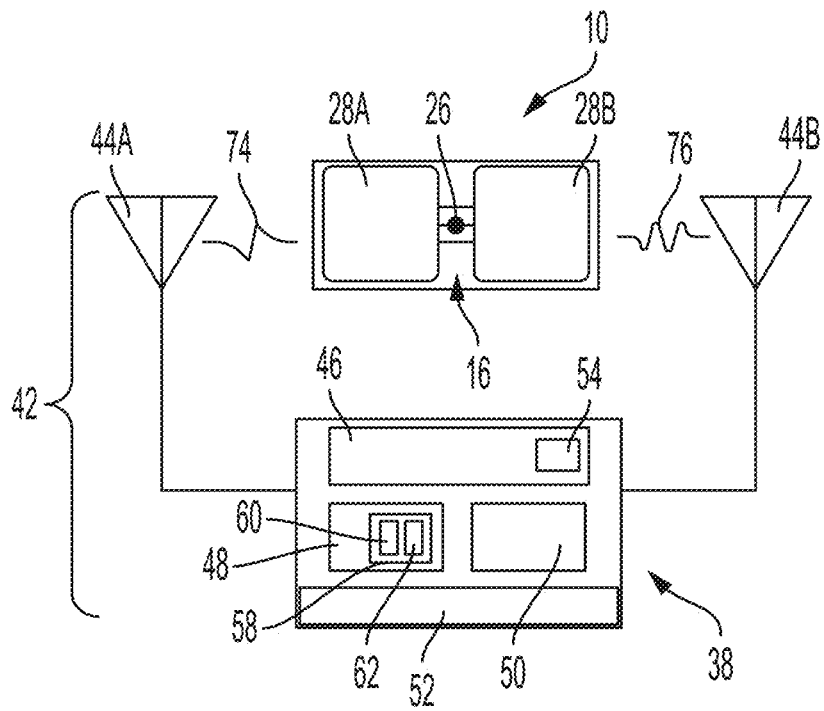
FIG. 9 shows a schematic view of an exemplary embodiment of a temperature monitoring system having two antennas, in accordance with the present disclosure.
Figure 10:
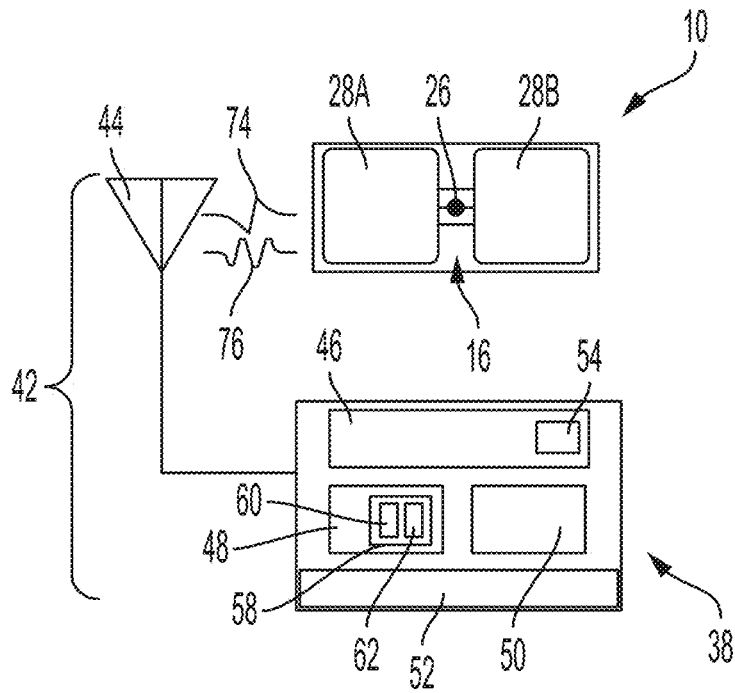
FIG. 10 shows a schematic view of an exemplary embodiment of a temperature monitoring system having one antenna, in accordance with the present disclosure.
Figure 11:
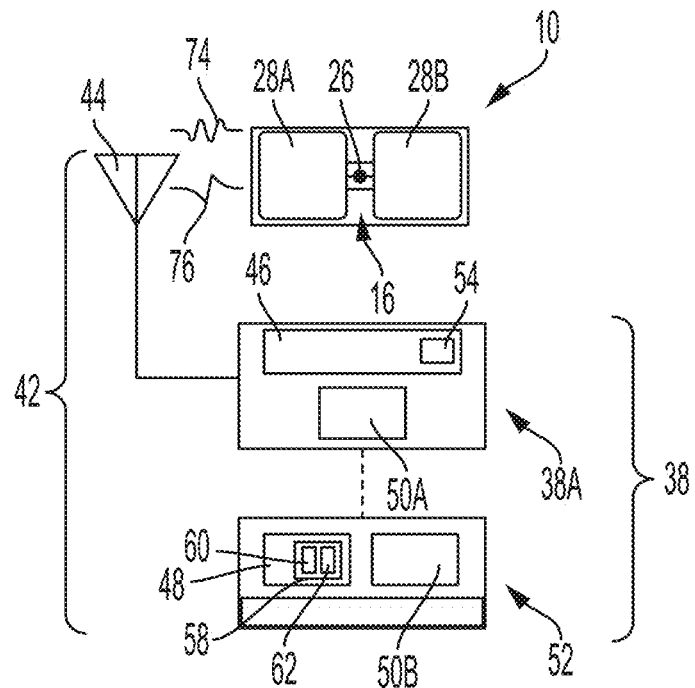
FIG. 11 shows a schematic view of a further exemplary embodiment of a temperature monitoring system, in accordance with the present disclosure.
Figure 12:
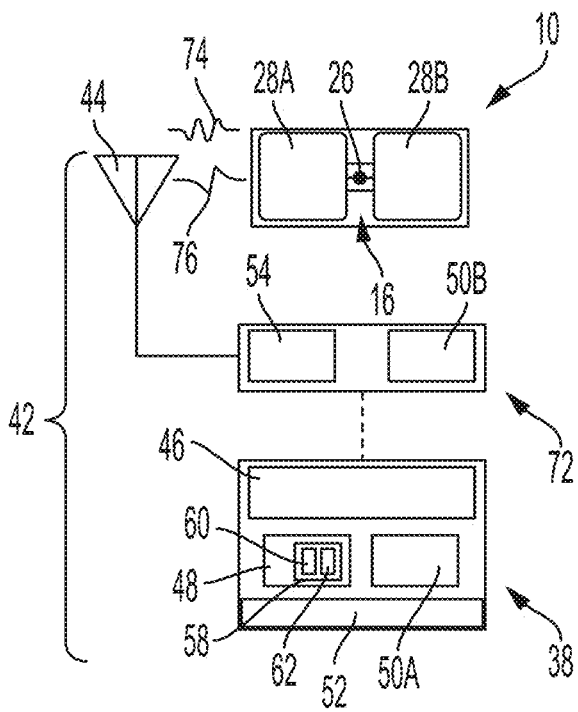
FIG. 12 shows a schematic view of a further exemplary embodiment of a temperature monitoring system, in accordance with the present disclosure.

Referring now to FIGS. 9-12, exemplary temperature monitoring systems 42 are shown. FIG. 9 shows an exemplary temperature monitoring system 42 that includes a reader unit 38 having two antennas 44A, 44B) and FIG. 10 shows an exemplary temperature monitoring system 42 that includes a reader unit 38 having a single antenna 44. Although FIGS. 11 and 12 show exemplary temperature monitoring systems 42 having a single antenna 44, it will be understood that the temperature monitoring systems 42 shown therein may alternatively include two antennas (or more), and the single-antenna configuration is shown for simplicity. Temperature monitoring systems 42 having more than one antenna may send and receive signals as shown and described in FIG. 9. In any embodiment shown in FIGS. 9-12, the exemplary temperature monitoring system 42 generally includes temperature sensor patch 10 and a reader unit 38. In any embodiment shown in FIGS. 9-12, as discussed above, the temperature sensor patch 10 includes a sensor circuit 16, which includes a RFID chip 26 and dipole antenna 24 having a first pole 28A and a second pole 28B. The sensor circuit 16 is passive and does not require a power source to detect or record temperature and/or temperature changes.

Figure 15:
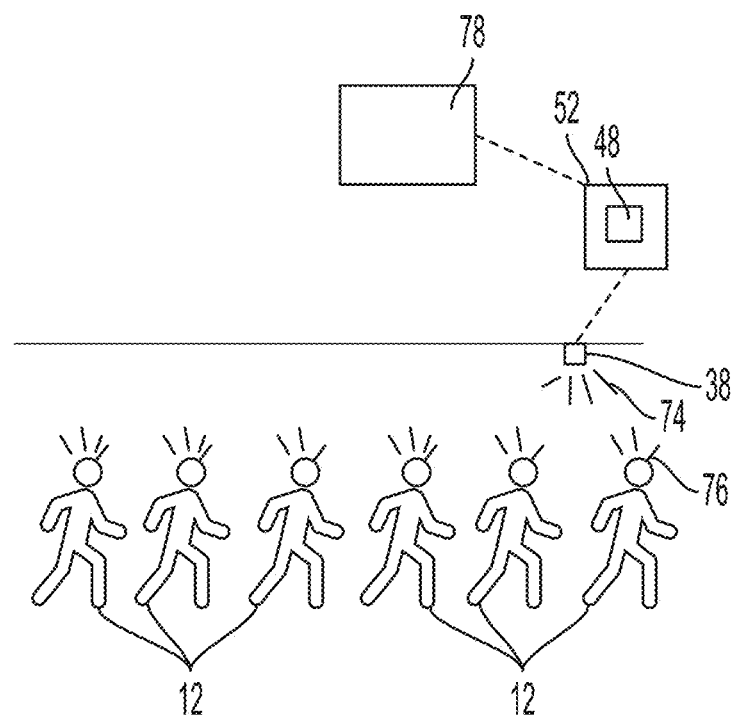
FIG. 15 shows a schematic view of a further exemplary embodiment of a temperature monitoring system in use, in accordance with the present disclosure
Figure 16:
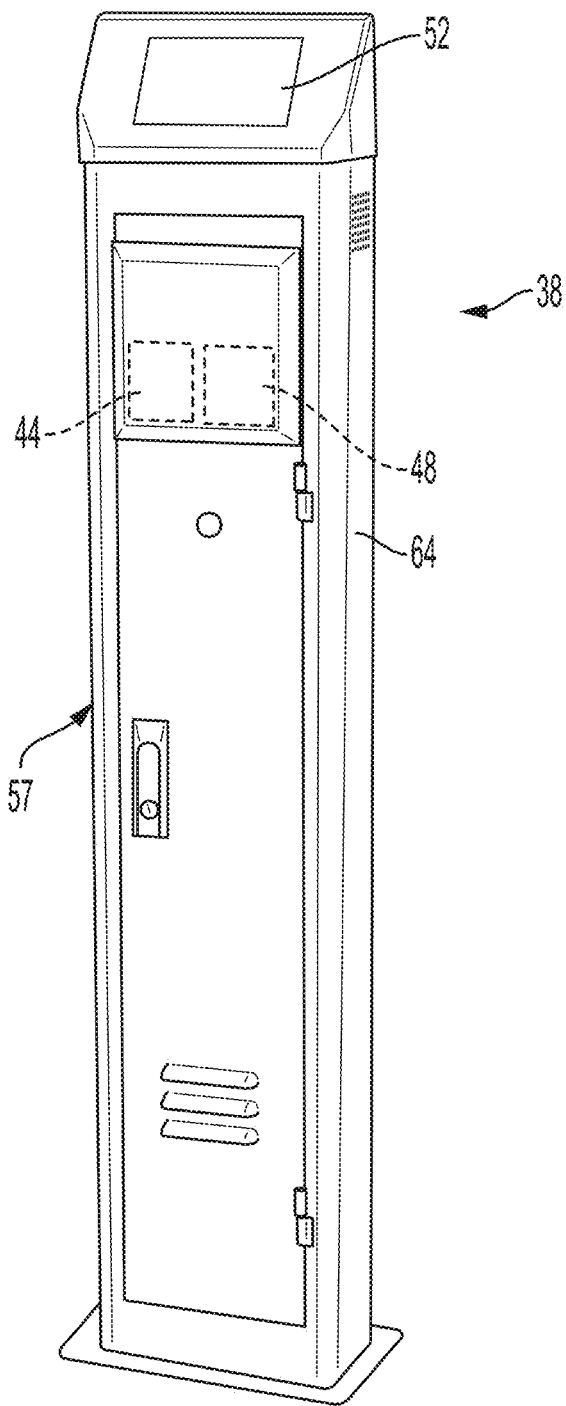
FIG. 16 shows an exemplary embodiment of a reader unit of a temperature monitoring system; in accordance with the present disclosure.

Continuing to refer to FIGS. 9-12, in one embodiment (for example, as shown in FIG. 9) the reader unit 38 includes a first antenna 44A, a second antenna 44B, a radiofrequency (RF) front end 46, a central processing unit (CPU) 48, and a power source 50 in electrical communication with the first and second antennas 44A, 44B, RF front end 46, and/or CPU 48. In other embodiments, (for example, as shown in FIGS. 10-12), the reader unit 38 includes a single antenna 44, a RF front end 46, a CPU 48, and a power source 50 in electrical communication with the antenna 44, RF front end 46, and/or CPU 48. In some embodiments (and regardless of the number of antennas), the exemplary temperature monitoring system 42 also includes at least one user interface 52, such as a screen, mobile device, tablet, touch screen, mouse, scrollwheel, keyboard, keypad, computer, smart phone, laptop, reading device, and/or other device for displaying and/or entering information and commands. The user interface(s) 52 may be physically separate from, but in electrical communication with, the reader unit 38 (for example, as shown in FIG. 11), and other configurations are contemplated (for example, as shown in FIG. 12); however, for simplicity all components external to the temperature sensor patch 10 may be collectively referred to herein as the reader unit 38. For example, regardless of the configuration of the temperature monitoring system 42, any components other than the temperature sensor patch 10 are collectively referred to as the reader unit 38. In some embodiments, the reader unit 38 is remote from (that is, not in contact with) the temperature sensor patch 10. In some embodiments, the reader unit 38 is at least one foot from the temperature sensor patch 10. In some embodiments, the reader unit 38 is up to 10 meters from the temperature sensor patch 10. In some embodiments the reader unit 38 is mounted to, affixed to, placed on, contained within, or otherwise associated with or supported by a structure 57, such as a doorway or portal (FIGS. 13 and 14), a ceiling or roof (FIG. 15), or a freestanding structure or device (FIG. 16).

Continuing to refer to FIGS. 9-12, in some embodiments, the RF front end 46 includes an RF signal generator 54. In one embodiment, the RF front end 46 is in electrical communication with the first and second antennas 44A, 44B, CPU 48, and/or power source 50 (for example, as shown in FIG. 9). Alternatively, in some embodiments, the RF front end 46 is in electrical communication with the single antenna 44, CPU 48, and/or power source 50. In one embodiment, the RF front 46 end includes one or more filters, amplifiers, and/or other components for transmitting, receiving, transforming, interpreting, and/or outputting or communicating signals. In some embodiments, all components of the reader unit 38 are contained within a reader unit housing 56. In other embodiments, the first and second antennas 44A, 44B (or antenna 44 in a single-antenna configuration, as shown in FIG. 10) are located outside of the reader unit housing 56 and in wired or wireless connection with the reader unit housing 56 and/or CPU 48 and other reader unit components (for example, as shown in FIG. 13).

Continuing to refer to FIGS. 9-12, in one embodiment, the CPU 48 includes processing circuitry 58 having a processor 60 and a memory 62. The memory 62 is in electrical communication with the processor 60 and includes instructions that, when executed by the processor 60, configure the processor 60 to receive RF signals from the temperature sensor patch 10 corresponding to temperature, correlate a frequency of an RF signal to a temperature to determine a real-time temperature of wearer of the temperature sensor patch 10, and output the determined temperature to the user interface(s) 52 (for example, to be displayed to a user in one or more screens or display components of the user interface(s) 52). For example, the CPU 48 may be programmed or programmable to run software to perform these tasks and to output the results to the user interface(s) 52 for communication to the user. For example, the software may present an interface for the user to connect the reader unit 38 to the Internet, local available communications networks, and/or other devices, to view charts, tables, and other graphics displaying data received from temperature sensor patches, or the like. However, it will be understood that other embodiments of the temperature monitoring system 42, including the reader unit 38, are contemplated.

Figure 13:
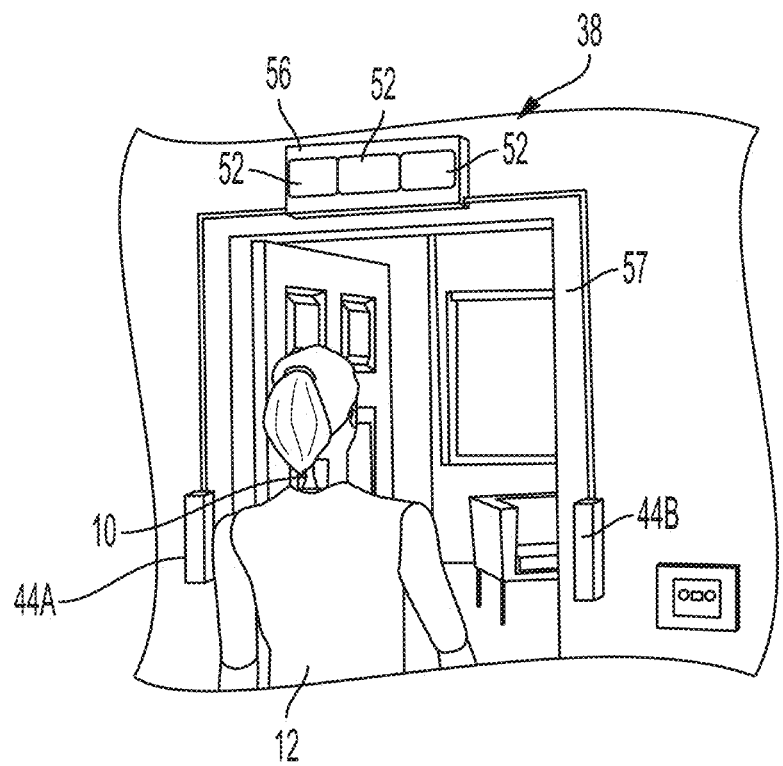
FIG. 13 shows an exemplary embodiment of a temperature monitoring system in use, in accordance with the present disclosure.

Continuing to refer to FIGS. 9-12, in one embodiment, the reader unit 38 includes the first and second antennas 44A, 44B, the power source 50, the RF front end 46, the RF signal generator 54, the CPU 48, and a user interface 52 (for example, as shown in FIGS. 9 and 13). In one embodiment, the reader unit 38 includes the antenna 44, the power source 50, the RF front end 46, the RF signal generator 54, the CPU 48, and the user interface 52 (for example, as shown in FIGS. 10 and 16). In one embodiment the reader unit 38 includes the CPU 48, which correlates received RF signals to temperature values, and one or more user interface devices 52 such as display screens, indicator lights (such as the red and green indicator lights shown in FIG. 13), speakers, or other alert device for indicating an alert condition, such as whether a wearer of a temperature sensor patch 10 has an elevated temperature and/or displaying the temperature value(s). In some embodiments, the reader unit 38 may be easily installed in an existing doorway, with the first and second antennas 44A, 44B (or antenna 44 in a single-antenna configuration) mounted on either side of the doorway and the reader unit housing 56 mounted therebetween, above the doorway. For example, the reader unit 38 may be a portal reader unit installed in a doorway or point of ingress or egress (or at any location experiencing human traffic), and may include an integrated user interface 52 with display(s) and/or a hand-held or portable user interface 52 that is in close proximity to (or at least within communication range from) and in wired or wireless communication with the reader unit 38. In one non-limiting example, as shown in FIG. 16, the reader unit 38, antenna(s) 44, user interface device 52 (such as a screen or touch screen), and other components are housed within or coupled to a housing 64 of a free-standing device 57. In some embodiments, the device 57 is configured to be connected to a power source to supply power to the reader unit 38, user interface(s) 52, and/or other components. For example, the device 57 may be configured to be plugged in to a standard 120-220 AC outlet. In some embodiments, the device 57 includes a dispenser or receptacle for unused temperature sensor patches. As discussed herein, it will be understood that the reader units 38 shown in FIGS. 9-16 may include two antennas (44A, 44B) or a single antenna (44), and other configurations of the temperature monitoring system other than those shown in these figures are contemplated.

Figure 14:
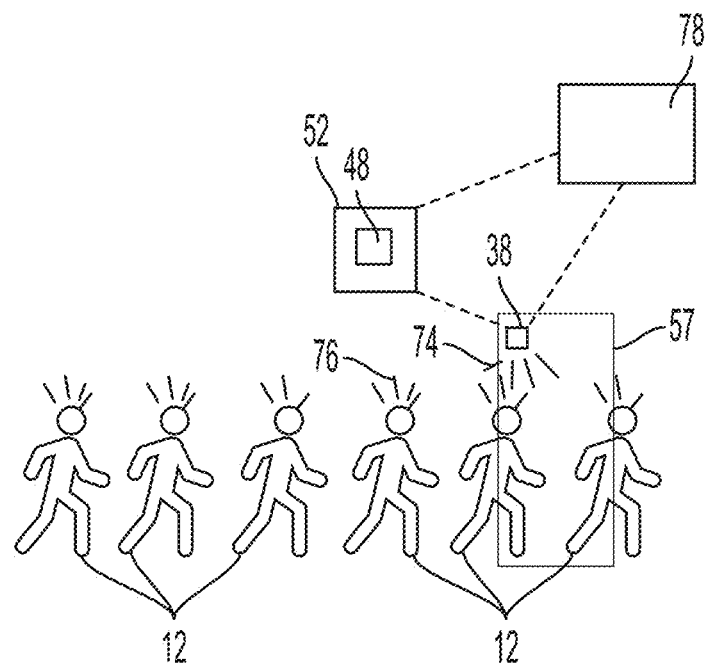
FIG. 14 shows a schematic view of a further exemplary embodiment of a temperature monitoring system in use, in accordance with the present disclosure.

Alternatively, as shown in FIG. 11, the reader unit 38 may include a reader unit device 38A that is physically separate from, but in wired or wireless communication with, a user interface 52, and the reader unit device 38A and the user interface 52 each includes its own power source. For example, the reader unit device 38A may perform one or more clean-up functions of a retrieved RF signal by the RF front end 46 (such as filtering, mixing, amplifying, or the like) and then transmit those signals to the user interface 52, wherein the CPU 48 of the user interface 52 determines and communicates real-time temperature to the user and/or performs other calculation, determination, and communication steps. Although in some embodiments any alert or alarm generated by the CPU 48 is communicated to the user through the user interface 52, in other embodiments the CPU 48 communicates an alert or alarm condition to the reader unit device 38A, which may also be configured to produce and communicate an alert or alarm to the user (for example, as shown in FIG. 14). In one embodiment, the reader unit 38 includes the RF front end 46, the RF signal generator 54, and a first power source 50A, and the user interface 52 includes the CPU 48 and a second power source 50B.

Alternatively, as shown in FIG. 12, the reader unit 38 includes the user interface 52 (the reader unit 38 and the user interface 52 are part of the same device), but the reader unit 38 is physically separate from, but in wired communication with, a transceiver 72. In one embodiment, the reader unit includes the RF front end 46, the CPU 48, the user interface 52 and a first power source 50A, and the transceiver 72 includes antenna(s) 44, an RF signal generator 54 and a second power source 50B. For example, the transceiver 72 may transmit unprocessed retrieved RF signal to the RF front end 46 of the reader unit 38, wherein the RF signals is processed by the RF front end 46 and/or passes directly to the CPU 48. Any alert or alarm generated by the CPU 48 may be communicated to the user through the user interface 52 and/or the reader unit 38. For example, if the user interface 52 is integrated with the reader unit 38, an alert or alarm may be communicated to the user through the reader unit 38. Alternatively, if the user interface 52 is remote from the reader unit 38, an alert or alarm may be communicated to the user through the reader unit 38 and/or the user interface 52 (for example, as described above regarding FIG. 11). An exemplary configuration of this system is shown in FIG. 15.

Continuing to refer to FIGS. 9-12, in some embodiments the reader unit 38 and/or user interface 52 includes a wireless communications module 70 configured to wirelessly transmit and/or receive data over a network to and/or from a central or remote server, remote computers and other devices, and/or other reader units 38. For example, the wireless communications module 70 may be configured to transmit and/or receive data via LoRa®, Wi-Fi®, Bluetooth®, Zigbee®, near-field communication (NFC), and/or other modalities now known or in the future developed.

Continuing to refer to FIGS. 9-12, in one non-limiting example of use, a wearer adheres a temperature sensor patch 10 to a suitable part of his or her body. For example, temperature sensor patches 10 may be sold individually, in bulk, in multiples by the box or package, made available in a dispenser, handed out, or otherwise made available to wearers. The RF signal generator 54 of the RF front end 46 of the reader unit 38 generates an interrogator RF signal 74 and transmits that interrogator signal 74 through the first antenna 44A (or through the antenna 44 in a single-antenna configuration, as shown in FIG. 10). In one embodiment, the interrogator RF signal 74 is in the order of micro Amperes. If multiple people each wearing a temperature sensor patch 10 pass within a range of the RF signal from the reader unit 38, the reader unit 38 will interrogate all of these temperature sensor patches 10.

Referring to FIG. 9, in one embodiment including two antennas 44A, 44B, the interrogator RF signal 74 is received by one or both poles 28A, 28B of the antenna 24 of the temperature sensor patch 10 from the first antenna 44A of the reader unit 38. Both poles 28A, 28B of the antenna 24 are configured to receive and transmit RF signals, and the sensor circuit 16 separates incoming and outgoing RF signals to prevent overlap. The interrogator RF signal 74 then passes through the sensor circuit 16 of the temperature sensor patch 10 to produce a retrieved RF signal 76 that contains temperature data, and the retrieved RF signal is then transmitted from the antenna 44 of the temperature sensor patch 10 to the second antenna 44B of the reader unit 38. Once received by the second antenna 44B of the reader unit 38, the retrieved RF signal 76 optionally may be filtered, amplified, or otherwise processed by the RF front end 46, and is then transmitted to the CPU 48. In embodiments wherein the reader unit 38 has a single antenna 44 that both transmits and receives signals, as shown in FIG. 10, RF signals are processed in a similar way as that described for FIG. 9, except that the interrogator RF signal 74 is transmitted from, and the retrieved RF signal 76 is received by, the single antenna 44 of the reader unit 38.

Referring to FIGS. 9-12, the CPU 48 is programmed or programmable such that the CPU 48 (CPU processing circuitry 58) is configured to receive a temperature sensor code value in the retrieved RF signal 76 that is proportional to the sensed temperature (for example, the temperature sensor code may be calculated by the sensor circuit 16 and stored in the memory 62), correlate that received temperature sensor code to a temperature of the wearer, and communicate or transmit the correlated temperature to the user interface(s) 52 for display to or alert of the user. Further, the CPU 48 is programmed or programmable to record a plurality of instantaneous temperatures over time, calculate a baseline average temperature over time based on the plurality of instantaneous temperatures over time, compare a new individual instantaneous temperature to the baseline average temperature over time, and generate an alert if the new instantaneous temperature exceeds or is greater than the baseline average temperature over time. The plurality of instantaneous temperatures over time may be from the same individual or from a plurality of individuals. Put simply, the reader unit 38 is configured to calculate a baseline average temperature for one or more individuals over time, and then compare a new instantaneous temperature (for example, a newly incoming reading from a temperature sensor patch 10) to that baseline average temperature over time to determine whether the new instantaneous reading is greater than the average and should potentially warrant the generation of an alert.

Continuing to refer to FIGS. 9-12, one of the problems with measuring skin temperature is that the skin temperature of the wearer is related to the core temperature, but is not equal to it. Thus, the CPU 48 is programmed or programmable to correlate skin temperature to actual core temperature and to correct for temperature variations of one individual and between individuals. Thus, in some embodiments the CPU 48 is programmed or programmable to correlate a retrieved RF signal 76 to a temperature, such as the temperature of the wearer's skin, and to calculate a core temperature of the wearer based on the temperature of the wearer's skin.

Continuing to refer to FIGS. 9-12, in one embodiment, the CPU 48 is further configured to transmit correlated temperatures, user data, wearer data, and/or other information to a central server 78 (shown in FIGS. 14 and 15) for further processing, storage, or the like. In some embodiments, each temperature sensor patch 10 includes a unique UID that is used to identify each temperature sensor patch 10. In one embodiment, this UID may be associated with a QR code that is displayed on the temperature sensor patch 10 and is readable and recognizable by the reader unit 38/CPU 48 and/or the UID may be otherwise recognizable by the reader unit 38/CPU 48. In some embodiments, the reader unit 38 is configured to receive RF signals from, and determine a correlated temperature of a plurality of, temperature sensor patches/wearers per second. In one non-limiting example, reader unit 38 may be configured to receive RF signals from, and determine a correlated temperature of, up to fifty (50) temperature sensor patches/wearers per second. In one non-limiting example, reader unit 38 may be configured to receive RF signals from, and determine a correlated temperature, of at least fifty (50) temperature sensor patches/wearers per second.

In one embodiment, the CPU 48 is also programmed or programmable to normalize the effect of environmental conditions such as ambient heat and humidity. If the CPU 48 determines or identifies a wearer having a temperature that is greater than a threshold value (for example, greater than approximately 99° F.) and/or within a threshold range (for example, approximately 102° F. (±3° F., or between approximately 99° F. and approximately 105° F.), the reader unit 38 may immediately generate an audible alarm through one or more speakers, a haptic alarm, a textual alarm displaying a description of the sensed temperature and location of wearer, a symbolic alarm displaying one or more cautionary or alert symbols, combinations thereof, and/or other suitable alerts. Likewise, in some embodiments the CPU 48 is programmed or programmable to recognize and account for acceptable variability within a particular individual and/or at a particular location (for example, reader unit portal, reader unit structure, or other measuring location), and to recognize a potential alert situation within a particular individual and/or at a particular location, even if a measured temperature would otherwise be recognized as normal. That is, the CPU 48 is programmed or programmable to calculate a baseline average temperature over time for that individual based on a plurality of instantaneous temperatures over time. For example, a person having an instantaneous temperature of 98.6° F. at a particular location might be recognized as a potential alert condition if the average instantaneous temperature of other individuals at that location is 95° F. Still further, the CPU 48 may be programmed or programmable to monitor an individual's temperature over time through temperature measurement data received over time from a temperature sensor patch that is unique to that individual. For example, if a person has an instantaneous temperature of one degree higher than a historical average over a selected period of time, the CPU 48 may recognize an alert condition. In contrast, if a historical data shows a similar trend, a false positive alert condition may be avoided. Thus, the temperature of each of many wearers may be continuously monitored in real time and the user(s) may receive immediate alerts once a temperature is detected that surpasses a threshold value, which allows the user(s) to quickly remove the detected wearer from the location/crowd and isolate the detected wearer for further testing and evaluation.

The temperature monitoring system 42 may also be used for contract tracing. As each temperature sensor patch 10 has a unique identification code (for example, UID), the path of the individual wearing a particular patch may be traced over a period of time as that individual passes through one or more reader unit portals or other measuring locations. For example, if an individual is recognized as having a higher-than-normal temperature ("flagged individual"), or a temperature that is otherwise recognized as a potential alert condition, the CPU 48 may review the identities of other temperature sensor patches that passed through the same reader unit portals/measuring locations to identify other individuals who may have come into contact with the flagged individual.

Additionally, as each temperature sensor patch 10 has a unique identification code (UID), the temperature sensor patch 10 may be used for multiple purposes related to the wearer. For example, the temperature sensor patch 10 may be used to store the wearer's digital ticket or pass information at a venue, as well as used to monitor the wearer's temperature. Additionally or alternatively, in some embodiments the temperature sensor patch 10 may be used as a payment system, to track school attendance, to track working hours, or the like. Additionally, because each temperature sensor patch 10 may be registered to a single individual, information relating to the wearer may be shared across platforms, including logistical data, access authorization data, medical data, monetary/banking/financial data, and/or ticketing data. For example, a temperature sensor patch 10 may be scanned as the wearer boards and disembarks a flight from San Francisco to Miami. This information may then be shared with other users of that information ("partner entities"), such as transportation providers, hotels, and venues, and may also indicate to those partner entities whether the wearer has a temperature that is outside of a threshold temperature or threshold temperature range. Further, this information may be shared without requiring the partner entities to invest in reader units or other infrastructure or equipment.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

As used herein, "and/or" means "and" or "or". For example, "A and/or B" means "A, B, or both A and B" and "A, B, C, and/or D" means "A, B, C, D, or a combination thereof" and said "A, B, C, D, or a combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings.

What is claimed is:

1. A passive temperature sensor patch, comprising: a sensor circuit, the sensor circuit including:
    a radiofrequency identification (RFID) chip;
    a dipole antenna, the dipole antenna including a first pole and a second pole, each of the first pole and the second pole having a width of approximately 33 mm and a height of approximately 34 mm; and
    a plurality of inductors extending between the first pole and the second pole, each of the plurality of inductors having a length of approximately 10.2 mm, wherein the width and the height of the first pole and the second pole and the length of each of the plurality of inductors providing optimization of a gain of the dipole antenna when the passive temperature sensor patch is affixed to a biological material; and
    a layer of base material, the sensor circuit being in the layer of base material and the layer of base material being configured to permit a signal transfer between the sensor circuit and a surrounding environment.

2. The passive temperature sensor patch of claim 1, wherein the RFID chip is an ultra-high frequency (UHF) RFID chip.

3. The passive temperature sensor patch of claim 2, wherein the RFID chip is tuned to use a UHF industrial, scientific, and medical (ISM) frequency band of 902 to 928 MHz.

4. The passive temperature sensor patch of claim 1, wherein a distance between outermost inductors of the plurality of inductors is approximately 10.3 mm.

5. The passive temperature sensor patch of claim 1, wherein the biological material is a multilayered substrate.

6. The passive temperature sensor patch of claim 5, wherein the multilayered substrate includes:
    a first layer that is skin;
    a second layer that is subcutaneous tissue;
    a third layer that is muscle; and
    a fourth layer that is bone.

7. The passive temperature sensor patch of claim 1, wherein the sensor circuit is configured such that the antenna has a gain of at least −8.4 dB.

8. The passive temperature sensor patch of claim 1, further comprising a coating layer on at least one surface of the layer of base material.

9. The passive temperature sensor patch of claim 1, wherein the RFID chip is configured to store personal identification data, monetary data, logistical data, access authorization data, medical data, and/or ticketing data.

10. A temperature monitoring system, the temperature monitoring system comprising:
    a passive temperature sensor patch including:
    a sensor circuit having a radiofrequency (RFID) chip and a dipole antenna, the dipole antenna including a first pole and a second pole, each of the first pole and the second pole having a width of approximately 33 mm and a height of approximately 34 mm;
    a plurality of inductors extending between the first pole and the second pole, each of the plurality of inductors having a length of approximately 10.2 mm, wherein the width and the height of the first pole and the second pole and the length of each of the plurality of inductors providing optimization of a gain of the dipole antenna when the passive temperature sensor patch is affixed to a biological material; and
    a layer of base material, the sensor circuit being in the layer of base material and the layer of base material being configured to permit a signal transfer between the sensor circuit and a surrounding environment; and
    a reader unit including:
    at least one antenna, the at least one antenna being configured to send and receive radiofrequency signals to and from the passive temperature sensor patch; and
    a central processing unit (CPU), the CPU being programmed to correlate a temperature sensor code value in a radiofrequency signal received from the passive temperature sensor patch to a temperature.

11. The temperature monitoring system of claim 10, wherein the passive temperature sensor patch is configured to be affixed to a skin of a wearer, the correlated temperature being a temperature of the wearer's skin.

12. The temperature monitoring system of claim 11, wherein the CPU is programmed to calculate a core temperature of the wearer based on the temperature of the wearer's skin.

13. The temperature monitoring system of claim 10, wherein the CPU is programmed to:
- record a plurality of instantaneous temperatures over time;
- calculate a baseline average temperature over time based on the plurality of instantaneous temperatures over time;
- compare a new instantaneous temperature to the baseline average temperature over time; and
- generate an alert if the new instantaneous temperature exceeds the baseline average temperature over time.

14. The temperature monitoring system of claim 13, wherein the new instantaneous temperature and the baseline average temperature over time are from a same wearer.

15. The temperature monitoring system of claim 13, wherein the new instantaneous temperature and the baseline average temperature over time are from different wearers.

16. The temperature monitoring system of claim 10, wherein the CPU is programmed to transmit temperature data to at least one partner entity.

* * * * *